US006448463B1

(12) United States Patent
Fischer et al.

(10) Patent No.: US 6,448,463 B1
(45) Date of Patent: Sep. 10, 2002

(54) NON-WOVEN APPLICATION FOR WATER DISPERSABLE COPOLYESTER

(76) Inventors: Carolyn A. Fischer, 1830 Oak Glen Dr., Stillwater, MN (US) 55082; Mai N. Haselman, Royal Court 9 M Kennedy Rd. Flat 35/B, WanChai (HK); Mark S. Hull, 12011 170th St., Marine on St. Croix, MN (US) 55047; Mark G. Katsaros, 6350 Barwick La., Duluth, GA (US) 30097; Mark S. Kroll, 3324 Katie La., Arden Hills, MN (US) 55112; Greg J. Van Lith, 5680 E. River Rd. Apt. 302, Fridley, MN (US) 55432; Sharf U. Ahmed, 1240 Silverwood Ct., Woodbury, MN (US) 55125; Andualem W. Emiru, 3165 Camelot Dr., Woodbury, MN (US) 55125

( * ) Notice: Subject to any disclaimer, the term of this patent is extended or adjusted under 35 U.S.C. 154(b) by 0 days.

(21) Appl. No.: 08/851,788

(22) Filed: May 6, 1997

Related U.S. Application Data

(63) Continuation-in-part of application No. 08/562,038, filed on Nov. 22, 1995, now Pat. No. 6,087,990.

(51) Int. Cl.[7] .............................. A61F 13/15; C08J 5/24; C08J 5/09; C08L 5/24
(52) U.S. Cl. ....................... 604/364; 524/539; 524/505; 524/292; 524/270; 525/74; 525/437; 525/420; 525/444; 604/385.01; 156/334; 442/392
(58) Field of Search .................................. 524/539, 270, 524/420, 444, 505, 292; 525/74, 437, 420, 444; 156/334; 442/392; 604/385.1, 364

(56) References Cited

U.S. PATENT DOCUMENTS

| | | | |
|---|---|---|---|
| 3,734,874 A | 5/1973 | Kibler et al. | |
| 3,779,993 A | 12/1973 | Kibler et al. | |
| 4,233,196 A | 11/1980 | Sublett | |
| 4,335,220 A | 6/1982 | Coney | |
| 4,719,260 A | * 1/1988 | Stuart, Jr. et al. | 525/74 |
| 5,143,961 A | * 9/1992 | Scholl et al. | 524/317 |
| 5,292,783 A | 3/1994 | Buchanan et al. | |
| 5,512,124 A | * 4/1996 | Hansen | 156/334 |
| 5,558,745 A | * 9/1996 | Conway et al. | 162/60 |
| 5,624,986 A | * 4/1997 | Bunnelle et al. | 524/270 |
| 5,744,538 A | * 4/1998 | Miller et al. | 524/539 |
| 6,034,168 A | * 3/2000 | Wang | 524/505 |

FOREIGN PATENT DOCUMENTS

| | | |
|---|---|---|
| EP | 0 333 515 A2 | 3/1989 |
| GB | 2295553 | 6/1996 |
| WO | WO 95/18191 | 7/1965 |

OTHER PUBLICATIONS

"Water Dispersable Hot Melt Adhesive Raw Material," Miller and George; Adhesive Age, Dec. 1995, pp. 30–32.

* cited by examiner

*Primary Examiner*—John G. Weiss
*Assistant Examiner*—Jamisue Webb

(57) ABSTRACT

This invention relates to water responsive thermoplastic compositions and articles constructed thereof. This invention particularly relates to thermoplastic copolyester compositions useful for the manufacture of disposable-articles such as disposable diapers and feminine napkins. More particularly, this invention relates to thermoplastic copolyester compositions that are useful as a raw material in the manufacture of nonwovens, barrier films or coatings and as well as for various improved hot melt adhesives compositions useful for incorporating hydrophilic features into disposable articles.

11 Claims, 3 Drawing Sheets

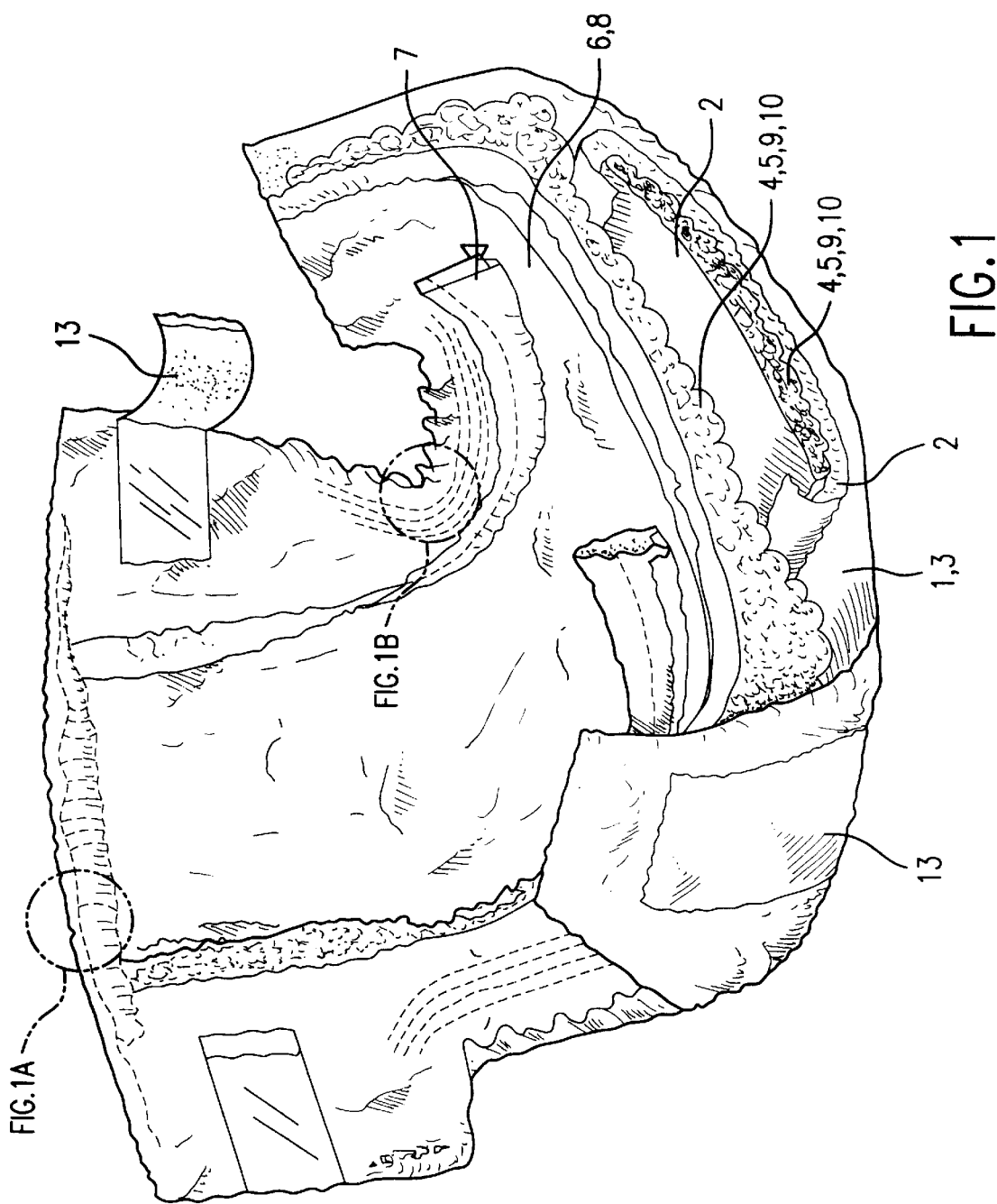

NON-WOVEN APPLICATION FOR WATER DISPERSABLE COPOLYESTER

RELATED APPLICATIONS

This application is a continuation-in-part of U.S. Pat. No. 6,087,990, Ser. No. 08/562,038 filed Nov. 22, 1995, which issued on Jul. 11, 2000.

FIELD OF THE INVENTION

This invention relates to water responsive thermoplastic compositions and articles constructed thereof. This invention particularly relates to thermoplastic copolyester compositions useful for the manufacture of disposable articles such as disposable diapers and feminine napkins. More particularly, this invention relates to thermoplastic copolyester compositions that are useful as a raw material in the manufacture of nonwovens, barrier films or coatings and as well as for various improved hot melt adhesives compositions useful for incorporating hydrophilic features into disposable articles.

BACKGROUND OF THE INVENTION

Currently in the nonwoven industry, with the exception of the pulp and super absorbent materials, disposable articles tend to be made of materials that are hydrophobic in nature. Water dispersible thermoplastic materials are gaining greater popularity as disposable article converters desire to incorporate hydrophilic features into their products.

WO 95/18191 teaches a water-dissipatable or dispersible adhesive composition useful in forming paper articles and other products that can be recycled through repulping in both neutral and alkaline media. The water-dispersible adhesive composition is preferably a hot melt adhesive that is a low molecular weight, branched copolyester containing a sulfonomer. Such polymers have recently become available under the tradename "Eastman AQ" copolyesters.

The "Eastman AQ" copolyesters are currently available in three experimental viscosity grades and one commercial viscosity grade, namely Eastman AQ 1350. Table I depicts typical physical property data of the neat copolyesters. In general, the neat copolyesters exhibits several deficiencies including cold flowability of the low molecular weight copolyesters, as well as poor sprayability, poor thermal stability and reduced water dispersibility of the higher viscosity materials.

The applicants have found that the "Eastman AQ" copolyesters, as well as similar water responsive copolyesters, have great utility in the nonwoven converting industry. When properly formulated, the disadvantages of the neat polyester can be overcome. Furthermore, the applicants discovered that it is possible to control the degree of water responsiveness such that the formulated adhesives may be useful for incorporating hydrophilic features into the substrates as well as the adhesives present yet not necessarily be water dispersible at one end of the spectrum, to using water dispersible copolyesters as a base raw material to make in-line substrates as well as adhesives to manufacture a completely flushable sanitary napkin or diaper at the other extreme.

When properly formulated, water responsive copolyesters are also suitable for adhesives compositions that improve acquisition and fluid management. Such adhesive compositions may be present to stabilize the core, improve the wicking of the core, for fixation of super absorbent polymers, or as a hydrophilic coating on a nonwoven. Additionally, water dispersible copolyesters have utility in formulating more traditional adhesive applications for construction, elastic attachment, or as garment attachment adhesives for securing a feminine napkin to an undergarment.

SUMMARY OF THE INVENTION

The present invention is a disposable article comprising at least two layers wherein at least one of said layers is a body fluid impermeable barrier having an interior and exterior surface and at least one second layer, wherein at least one of said second layers is a body fluid permeable cover attached to said interior surface of said barrier wherein at least one layer comprises a water dispersible copolyester. The disposable article may also optionally contain, an absorbent layer, or at least one tissue layer, or at least one elastomeric material, or at least one superabsorbent polymer material disposed between said barrier and cover, or at least one adhesive bonding at least one layer to an adjacent layer or material. The water dispersible copolyester may be present as a raw material in the manufacture of permeable covers such as nonwoven, body fluid impermeable barrier films, fastening systems for tapes or fastening systems such as Velcro®, and elastomeric features such as elastic leg and waist attachments, as well as standing leg gathers. Furthermore, water responsive copolyesters may be present in various traditional adhesive compositions intended to bond such substrates as well as for adhesives that improve acquistion and fluid management. The use of the water dispersible copolyester may be for any one or all of these nonwoven applications as well as numerous combinations of such applications.

The improved hot melt adhesive composition comprises at least 25% of at least one water dispersible copolyester and up to about 75% of at least one ingredient selected from the group consisting of compatible polymers, tackifiers, plasticizers, and waxes. A solid plasticizer is a preferred plasticizer. Preferably, the copolyester has a viscosity less than about 40,000 cps at 177° C., more preferably less than about 7,000 cps at 177° C. To increase the strength of the thermoplastic composition, a copolyester having a viscosity of about 28,000 cps or greater at 177° C. is combined with a copolyester having a viscosity less than about 7,000 cps at 177° C. The improved hot melt adhesive is sprayable, resists cold flow, and exhibits good thermal stability.

Although the hot melt adhesives exemplified herein are targeted for various nonwoven applications, the hot melt adhesive compositions may also be employed in a wide varierty of other uses as are known in the art. Examples of such include water repulpable adhesives for bookbinding, case and carton sealing, bag sealing, roll wrapping and tissue plybonding, as well as remoistenable adhesives for envelope seals and other labeling applications. The inventive pressure sensitive adhesives described herein have been found to have particular utility for bonding to moist surfaces. This aspect is advantageous for bottle labeling as well as for medical applications for bonding to skin, provided the water dispersible copolyester has the proper FDA clearance for such applications.

The preferred ingredients of the adhesive composition is dependent on the intended use of the adhesive and will be exemplified in the examples set forth in the specification.

BRIEF DESCRIPTION OF THE DRAWINGS

FIGS. 1 and 2 are representative disposable absorbent articles. FIG. 1 depicts a typical disposable diaper, whereas FIG. 2 depicts a feminine napkin.

DETAILED DESCRIPTION OF THE INVENTION

Figure 1B:
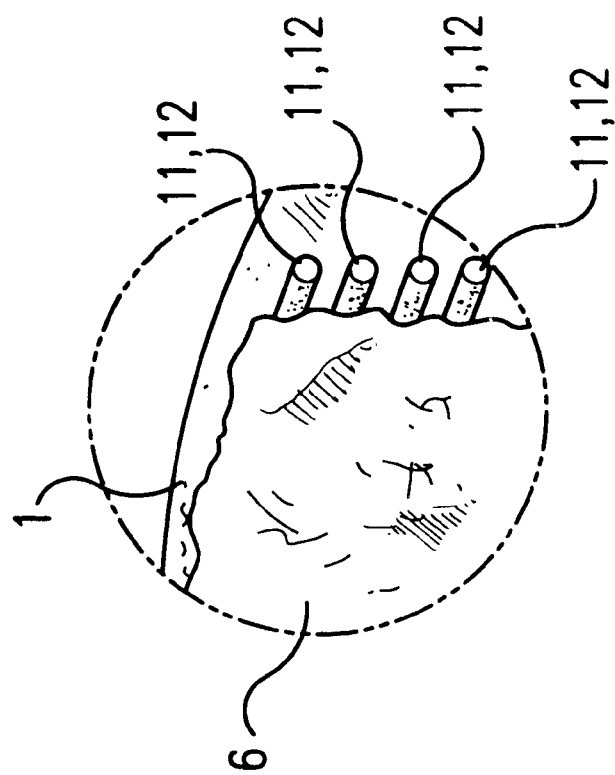
FIGS. 1A and 1B are enlargements of the waist and leg portions in FIG. 1.
Figure 1A:
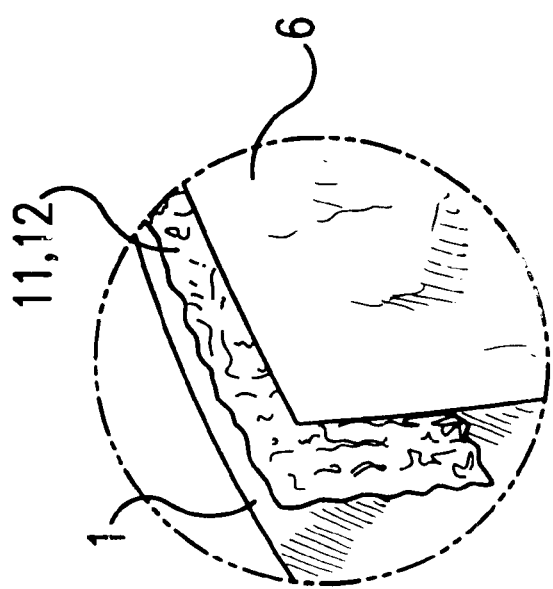
Figure 2:
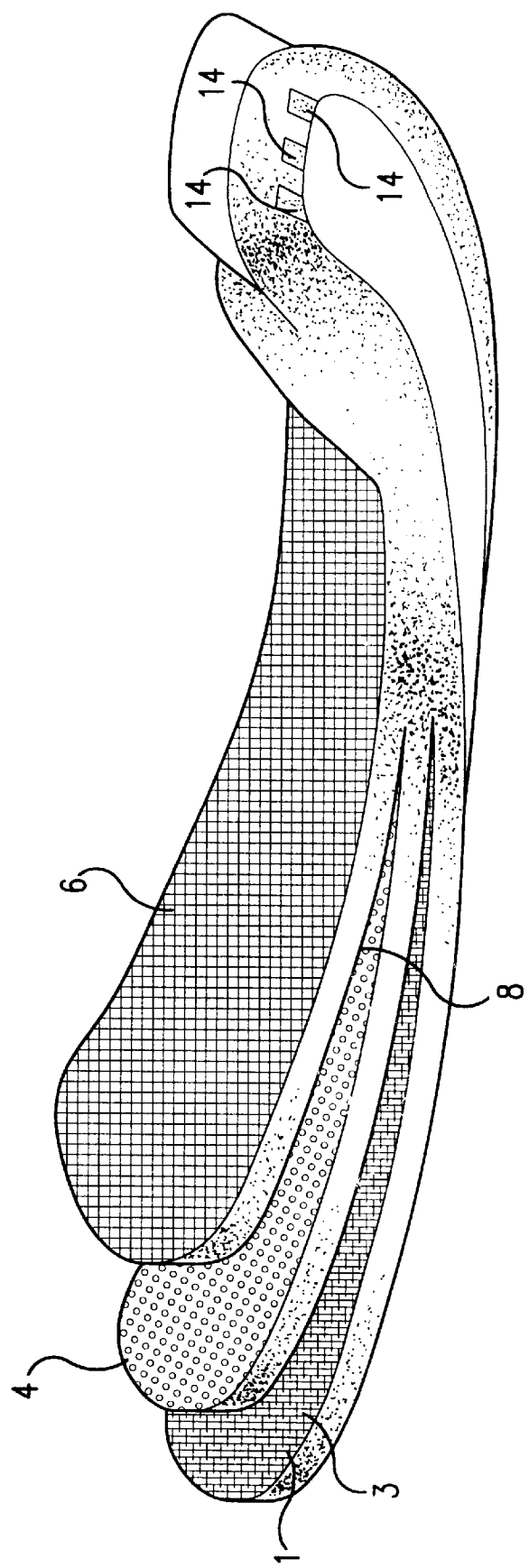

To appreciate the breadth of the present invention, it is necessary to discuss each substrate as well as existing and potential adhesive applications in a typical disposable article. FIGS. 1 and 2 are provided for this purpose and are not intended to limit the invention with respect to product design, substrates, materials, adhesive applications, etc. Although a disposable diaper and feminine pad are exemplified, this invention also extends to other disposable products such as hospital pads, surgical drapes and gowns, and the like which either contain a similar substrates or have a similar function. Surgical drapes and gowns typically consist of only two layers, namely a permeable cover and an impermeable barrier.

The exterior of a disposable absorbent article is typically a body fluid impermeable barrier (1). Such barriers are typically provided as a film roll good and are generally comprised of polyolefins such as polyethylene or ethylenic copolymers such ethylene-vinyl acetate. Alternatively, the barrier film could be made in-line by coating a thermoplastic composition to a carrier material such as a nonwoven. Water responsive copolyesters, are suitable as a raw material for a readily water dispersible backsheet regardless of the method of manufacturing such. This is of particular interest for manufacturing flushable sanitary napkins. The water dispersible copolyester may be used uncompounded or preferably compounded to improve processability to form a continuous film of a single composition. Due to cost considerations, it may be more beneficial to form a matrix of water dispersible copolyester surrounding portions of more conventional insoluble polymers. Any known process suitable for making such a film can be employed.

The barrier is typically bonded to a layer of tissue (2) in the interior portion of the diaper with a construction adhesive (3). The construction adhesive may be applied as a multi-bead application or more commonly applied by spiral spray or melt-blown spray techniques. For flushable disposable absorbent products, at a minimum, all the adhesive applications must substantially maintain their bond in the presence of body fluids during usage, yet most of the adhesive must readily disperse in tap water to insure easy passage into the waste water stream. Preferably, the substrates, including the barrier, elastomeric materials, and the body fluid pervious topsheet, should also be readily water dispersible in tap water, of which water responsive copolymers are suitable. Due to the density of the copolyester being greater than water, it is believed that the adhesives and other substrates comprising water responsive copolyester can be easily separated with existing waste water treatment techniques.

The absorbent core (4) is typically of fibrous pulp and often contains at least one granular super absorbent polymer (SAP) (5). The absorbent is sandwiched between the tissue layer, or alternatively the barrier layer if a tissue layer is not present, and a body fluid pervious cover (6). The body fluid pervious cover is typically polypropylene based nonwoven or aperatured polyolefin, both of which are hydrophobic in nature. Such covers are often treated with a surfactant to aid in acquisition by preventing body fluids from pooling on the cover surface. In disposable absorbent articles having standing leg cuffs (7), which are intended to improve containment by creating a physical hydrophobic barrier, often two nonwovens are needed, namely a surfactant treated or hydrophilic nonwoven for the target acquisition zone and a hydrophobic nonwoven for the standing leg cuffs. Water responsive copolyesters can be used as a raw material in the formation of the cover or alternatively used as a coating on existing covers to eliminate the need for surfactants. Surprisingly, although the copolyesters and thermoplastic compositions containing such, are insoluble in body fluids, the copolyesters are hydrophilic, and thus responsive with respect to body fluids. Hydrophilic, in this sense, means that body fluids exhibits a relatively low contact angle with respect to a continuous coating of the copolyester, or composition containing such.

The copolyester may be used alone or in combination with other polymers to create a variety of useful properties in the resulting web. Preferably the copolyester is compounded to improve processability and reduce cold flow tendencies. By combining the water dispersible copolyester with conventional insoluble polymers such as polyethylene, polypropylene, polyester, and polyamide sequentially during the web forming process, the resulting web will have a water dispersible matrix. Preferably, the insoluble polymer is applied to form a discontinuous web. The water dispersible copolyester in then applied to the discontinuous regions such that the resulting web dissolves at the locations where the copolyester is present leaving small portions of the insoluble portions intact. Alternatively, the water dispersible copolyester may be applied as a continuous phase with discontinuous regions of the insoluble polymer. These techniques create a low cost flushable web. By combining the water dispersible copolyester with at least one insoluble polymer simultaneously, it is possible to create webs having hydrophilic character that are not dispersible in water.

The cover is typically bonded to the absorbent core with a construction adhesive. Commonly, this construction adhesive is of the same composition used to bond the barrier. However, since this adhesive application has a different function than that of the adhesive bonding the barrier, this adhesive application will be denoted as the "cover construction adhesive" (8) for purposes of this invention. Traditional construction adhesives are hydrophobic in nature and are therefore blamed for interfering with the acquisition through the cover into the absorbent core. However, it is vitally important that the cover maintains in intimate contact with the absorbent core during use to prevent body fluids from pooling and consequently causing leakage problems. Therefore, eliminating the cover construction adhesive is not an option. Water responsive copolyesters offer a solution to this particular problem. Traditional adhesives can be made hydrophilic with relatively small concentration of at least one water responsive copolyester. By increasing the concentration of water dispersible material, such adhesives can be made increasingly hydrophilic to the extent that they substantially maintain their bond in the presence of body fluid yet readily disperse in tap water.

Optionally, the pulp may be stabilized with a core stabilization adhesive (9). The use of core stabilization adhesives is discussed in detail in EP 422 108 B1 and EP 410 412 B1, both assigned to H. B. Fuller, incorporated herein by reference. Prior art adhesives tend to be hydrophobic in nature. The use of a hydrophilic core stabilization adhesive comprising water responsive copolyester provides an additional benefit of enhanced acquisition.

Hydrophilic adhesives are also essential to SAP fixation (10). Presently, the SAP is typically not adhesively fixed in place due to concerns that an adhesive will interfere with the absorption. However, as disposable absorbent product manufacturers reduce the pulp and thickness of their products and in turn increase the amount SAP, fixation of the SAP becomes increasingly important. Hydrophilic adhesives based on water responsive copolyesters are very desirable for this application. Preferably, such adhesives are nearly instantaneously responsive to aid in the absorption of the SAP.

At the periphery of a disposable absorbent article, the barrier is usually adhesively bonded to elastomeric materials (11) with elastic attachment adhesives (12) to improve the fit and reduce leakage at the waist and around the legs. Both the elastomeric materials as well as the adhesives for bonding such elastomeric materials can be made water dispersible with the use of water responsive copolyesters.

On the exterior of the barrier film is a fastening system (13). In disposable diapers, the fastening system is typically tape or a mechanical hook and loop and similar fastener means such as Velcro®. On feminine napkins the fastening system is usually a positioning adhesive (14). The positioning adhesive is typically pressure-sensitive in nature and covered with a release paper that is removed upon use, exposing the adhesive for attachment to an undergarment. Water responsive copolyesters have utility as an adhesive composition for the tape, both for the adhesive and the backing as well as the positioning adhesive. Alternatively, the higher molecular weight copolyesters may be suitable as a raw material in making mechanical fastening means.

The Thermoplastic Composition

The most critical ingredient of the thermoplastic composition of the present invention is at least one water dispersible copolyester, present in an amount from about 25 to 100% by weight. Water dispersible copolyesters are those in which ionic moieties or water sensitive reactants such as ethylene glycol are incorporated into the backbone. Alternatively, the ionic moieties may be grafted onto the backbone. The structure of such copolyesters are described in Miller et al., WO 95/18191, incorporated herein by reference. The "Eastman AQ" copolyesters, as taught by Miller, incorporate ionic moieties by copolymerizing 5-sodiosulfoisophthalate units into a polyester backbone.

The concentration of water dispersible copolyester present in the thermoplastic composition is dependent on the particular viscosity grade and the amount of hydrophilic character or water dispersibility that is desired. In general, the higher viscosity copolyesters and/or low concentrations of the low viscosity copolyesters materials are useful in thermoplastic compositions having hydrophilic character which are not necessarily readily water dispersible. Alternatively, the lower viscosity materials at higher concentrations are preferred for compositions that are readily dispersible in tap water for flushable articles. By blending the different viscosity grades of the "Eastman AQ" copolyesters, it is surprisingly possible to increase the strength without sacrificing water responsiveness.

Second Polymer

Due to the deficiencies in the neat polymer, it is often desirable to add a second compatible polymer at concentration up to about 20% by weight to increase the cohesive strength, improve the sprayability, and/or reduce the cold flow tendencies. This second polymer may be any compatible elastomer, such as a thermoplastic block copolymer, an amorphous or crystalline polyolefin such as polypropylene, polybutylene or polyethylene; and ethylenic copolymers such as ethylene-vinyl acetate, ethylene-methyl acetate, and mixtures thereof. Preferably, for improved pressure sensitive adhesives, a block copolymer such as Kraton D-4158 (30% styrene radial high Mw SBS), Kraton D-1117 (40% diblock, 17% styrene linear SIS), Kraton D-6428 as well as a variety of other known block copolymers are employed in combination with the copolyester.

Tackifying Resin

The thermoplastic compositions of the invention may contain a tackifying resin. Tackifying resins are present in amounts up to about 60% by weight. Preferably, the resin is present in an amount from about 20 to about 50 weight percent. The preferred tackifying resins useful in the adhesives of the invention comprise resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers are also useful in the adhesive of this invention. Representative examples of useful hydrocarbon resins includes alpha-methyl styrene resins and suitable derivatives thereof, branched and unbranched $C_5$ resins, $C_9$ resins, $C_{10}$ resins, as well as styrenic and hydrogenated modifications of such. The article by Davis, "The Chemistry of $C_5$ Resin," discusses synthetic $C_5$ resin technology. Tackifying resins range from being a liquid at ambient temperatures to having a ring and ball softening point of about 135° C.

Plasticizers

A plasticizer is broadly defined as a typically organic composition that can be added to thermoplastics, rubbers and other resins to improve extrudability, flexibility, workability, or stretchability.

Plasticizers may be used in the adhesive of this invention at concentrations up to about 50% by weight. Preferably, the plasticizing agent is a solid at ambient temperature with a softening point above 60° C. and belongs to the class of plasticizers including cyclohexane dimethanol dibenzoate. The beneficial properties of solid plasticizers is surprising and contrary to the teachings of Miller. Although a 1,4-cyclohexane dimethanol dibenzoate compound commercially available from Velsicol under the tradename Benzoflez® 352 is exemplified, any plasticizer that will recrystallize in the compounded thermoplastic composition is suitable. Other plasticizers that may be suitable for this purpose are described in EP 0422 108 B1 and EP 0 410 412 B1, both assigned to H.B. Fuller Company, incorporated herein by reference. When combined with the Eastman copolyester these plasticizers exhibit the unique ability to vastly improve the processability in the molten state, yet not interfere with the dispersibility once cooled and solidified.

Other preferred plasticizers include dipropylene glycol dibenzoate (Benzoflex® 9-88), diethylene glycol dibenzoate (Benzoflex® 2-45), diethylene glycol/dipropylene glycol dibenzoate (Benzoflex® 50), propylene glycol dibenzoate (Benzoflex® 284), polypropylene glycol dibenzoate (Benzoflex® 400), polyethylene glycol dibenzoate (Benzoflex® P-200), etc.

Other suitable plasticizers include hydrocarbon oils, polybutene, liquid tackifying resins, and liquid elastomers. Such oils are primarily hydrocarbon oils, and are paraffinic or naphthenic in character. The oils are preferably low in volatility, transparent and have as little color and odor as possible. The use of plasticizers in this invention also contemplates the use of olefin oligomers, low molecular weight polymers, vegetable oils and their derivatives and similar plasticizing liquids.

Wax

The adhesives of this invention may comprise a wax present in amounts up to about 20% by weight, more preferably in amounts ranging from about 1 to about 10% by weight. The wax is added to modify the viscosity, reduce the tack, and improve the humidity resistance. Preferably, the wax is polar in nature such as amide waxes. Other useful waxes include paraffin waxes, microcrystalline waxes, Fischer-Tropsch, polyethylene and by-products of polyethylene.

As is known in the art, various other components can be added to modify the tack, color, odor, etc., of a hot melt adhesive. It is generally preferred that the other components or ingredients should be relatively inert and have negligible effects upon the properties contributed by the copolyester, tackifying agent, and plasticizer. Antioxidants and other stabilizing ingredients can also be added to protect the adhesive from various heat and light induced degradation, but are not essential to the compositions of this invention.

TEST METHODS

T-peels

This test method describes how to measure the removal force of an adhesive surface bonded to a fabric substrate.

Material and Equipment:

1. Mechanical roll-down device with 4½ lb. roller.

Available through: Engineering Service, Glenview Ill. 60025

2. Slip Peel Tester

Available though: Instrumentors, Inc., Cleveland, Ohio 44136

The first step is to prepare hot melt coated adhesive films on Mylar or polyethylene film using a suitable coating device at an appropriate application temperature. During preparation of the adhesive film, the adhesive surface is covered with release paper to facilitate handling. The coat weight is checked targeting 50 g/m2+/−3 g/m2.

The adhesive coated mylar is cut into 1" width strips 4 inches in length in machine direction. At one end of each strip, fold approximately ¼" of the strip onto itself to create a grip. Remove the release paper and place the adhesive surface in contact with a knit cotton fabric. Place the composite on the mechanical roll-down device, and allow the roller two passes over the sample, one forward and one back. A timer is activated and the sample is placed into the jaws of the slip-peel tester. The adhesive coated strip is placed into the mobile jaw and the 1.5" strip in the stationary jaw. No more than 1 minute after the sample has been removed from the roll-down device, the sample is peeled at 12 inches per minute, averaging over 10 seconds. The procedure is repeated five time, recording the average T-peel value and noting any legging or transfer. The T-peel values are reported in grams per lineal inch. For the stressed T-peel the adhesive coated surface in placed in contact with a Tricot nylon fabric, conditioned in a 105° F. oven for 45 minutes under a pressure of 100 g/in$^2$ and conditioned for an additional 15 minutes at ambient temperatures prior to peeling.

Multi-bead & Spray

This procedure covers the method for applying and testing adhesives for multi-bead and spiral spray construction.

Adjust the hot melt applicator and laminator to proper settings as follows:

| | |
|---|---|
| Temperature: | 300° F.–350° F. |
| Air Temperature: | 350° F.–380° F. |
| Nip Pressure | 30 psi |
| Application Rate | 4 mg/in$^2$ (spiral spray) |
| | 1.4 mg/in (multi-bead) |
| Web Speed | 400–500 ft/min |

Apply the adhesive to a polyethylene backsheet material, nipping to nonwoven. During the run, ten 2"×8" strips of release paper cross directional across the web to serve as starting points for the T-peel evaluation. Cut 10 samples one bead or one spray spiral in width by 3" in length. Run T-peels on a slip/peel tester, Instron or other suitable measuring device at 12"/min. Report the average of 5–10 samples.

Wet Strength

Hang on end of a 4" length segment of a spiral spray bond in a 180° static shear tester. Hang a 10 g weight on the other end. Spray the bond with test solution until saturated. Activate a timer recording the time at which the bond failed.

Repulpability

The adhesives of examples 10–16 were tested in accordance with the "Modified Stone Container #2" test method. The adhesives were used to bond paper at a weight of 1.0 g of adhesive per 39.0 g of paper. The coated paper is cut into 1"×1" pieces and placed in the disintegrator. 1960 ml of 73° F. water is added and the mixtures is agitated for 25 minutes. Hand sheets are formed by pouring 100 ml and 200 ml of the pulp water mixture onto a sheet mold. The sheets are pressed, dried and inspected for visible matter. "P"—Pass—No particles or other matter is visible to the eye. "F"—Fail—Particles or other matter are visibly detected.

The water responsive thermoplastic compositions and articles constructed thereof can be further illustrated by the following non-limiting examples.

Barrier Film

An in-line film was made by coating the 0.4 IV Eastman copolyester onto a nonwoven substrate. The material was coated using a noncontact slot coat application method described in detail in H.B. Fuller's copending PCT application, Application No. EP 95/0065 filed Feb. 23, 1995, incorporated herein by reference. The molten 0.4 IV material was coated at 160° C. at a distance of 1 mm from the substrate utilizing a 22 cm×0.3 mm shim wherein the adhesive exits the shim in a substantially horizontal direction with respect to the substrate which is traveling in an upward direction. A flow rate of 42 g/min was used in combination with a line speed of 30 m/min and a pump pressure of 65 bar to create a continuous film having a coat weight of 6 g/m$^2$. The diameter of the coating roll is preferably about 15 to 50 mm in diameter with the nozzle slightly above center of the coating roll such that the angle at which the adhesive contacts the substrate is less than about 60° and the substrate is moving away from the nozzle. Preferably, the coating head is optimized for even flow and distribution of the adhesive over the entire width of the application. One of ordinary skill in the art could make such adjustments.

An 8"×8" sheet of coated nonwoven was secured to the lip of a 1 pint glass jar such that a depression was present of sufficient size to hold 2 ounces of test fluid. Leakage observations were made with deionized water and 0.9%

NaCl solution test fluid as well as with uncoated nonwoven initially and then again after 1.5 hours.

| Sample | Deionized Water | .9% Saline |
|---|---|---|
| Adhesive Side Up | No leakage detected* | No leakage** |
| Adhesive Side Down | Leaked within 1–3 min. | No leakage |
| Uncoated Nonwoven | No leakage detected | Not Applicable |

*The bottom surface of the nonwoven was wet.
**The bottom surface of the nonwoven was dry.

The nonwoven coated with the Eastman 0.4 IV was found to be impervious to a 0.9% monovalent NaCl saline test solution, yet deionized water was able to penetrate the copolyester coating. The uncoated nonwoven itself has some barrier properties. As such, when the adhesive is on top, the adhesive disperses in the deionized water yet is unable to penetrate the nonwoven. When the adhesive is on the bottom, the coating readily disperses and draws the water through the nonwoven. The applicants surmise that the barrier properties can be further improved upon by compounding the copolyester with a tackifier, plasticizer and/or a wax. Furthermore, a second polymer or a blend of a low viscosity copolyester with a high viscosity copolyester may be preferred to improve the cohesive integrity of the body fluid impervious film or coating.

Although the coating method described above is believed to be preferred in order to manufacture a low gauge in-line continuous film, other coating methods may also be suitable. The barrier film may also be made off line by any known film forming technique. Providing the Eastman copolyester materials as a roll good will be very difficult due to the blocking tendencies of the neat polymer. To overcome these difficulties, the copolyester may be blended with waxes, EVA, polyethylene, polypropylene or other materials to reduce blocking tendencies. Preferably, in order to maintain water dispersible properties, the film should contain at least 50° water dispersible materials, of which the Eastman copolyesters may be used alone or in combination with other water dispersible materials.

Pervious Cover

The Eastman copolyesters may be used as a raw material to form a nonwoven. The materials are best suited to form nonwovens in-line. Alternatively, the Eastman copolyesters can be incorporated into a web by any suitable known web forming technique. As in the case of the barrier film, the neat copolyesters are undesirable. The 0.2 IV material is sprayable, yet due to its lack of cohesive strength and cold flowability it cannot form a stable web. The 0.4 IV and higher viscosity grade materials do not spray well and still suffer from blocking tendencies. As in the case with the barrier coating, the applicants surmise compounding a low viscosity copolyester with a high viscosity copolyester in combination with a small concentration of tackifier, plasticizer, and/or wax would overcome such problems. Additionally, other polymers may be employed to improve the strength and reduce cold flow tendencies. This compounded material may be used as the sole base material for forming a nonwoven web.

Alternatively, the copolyester may be used in smaller concentrations in combination with more conventional nonwoven base materials such as polyethylene, polypropylene, polyamides or polyesters to create nonwoven webs ranging from being hydrophilic yet not necessarily water dispersible to those which are readily water dispersible.

Alternatively, a hydrophobic nonwoven may be coated with a thermoplastic composition comprising a water responsive copolyester. The 0.2 IV "Eastman AQ" material was applied to the interior surface of a hydrophobic nonwoven using meltblown adhesive spray equipment at a temperature of 300° F. The coated nonwoven was then placed on top of an absorbent medium such that the coating was in direct contact with the absorbent. Synthetic urine (0.9% NaCl) was poured on the uncoated surface. The fluid was readily absorbed by the coated nonwoven. In contrast, when synthetic urine was applied to the control sample, the fluid pooled on the surface. Although this example demonstrates the utility and effectiveness of a hydrophilic composition comprising the Eastman copolyester, the applicants anticipate that over time the 0.2 IV neat material will migrate through the cover or into the absorbent core and thus lose it's effectiveness over the normal shelf life of an absorbent product (1 year). Therefore, the applicants anticipate further compounding the Eastman copolyesters with other materials as in the case of the barrier film.

Core Stabilization

Example 1 depicts a core stabilization adhesive. The adhesive composition is flowable for a period of time after it has been applied. Upon recrystallization of the Benzoflez 352, the adhesive stiffens, diminishing in cold flow properties and substantially loses its pressure sensitivity. This type of delayed crystallization is well suited for pulp bonding since the initial flowability of the adhesive is conducive to mechanical bonding of the pulp fibers. The loss of pressure sensitivity also makes this adhesive composition useful for a pervious cover construction adhesive. Typical pressure sensitive adhesives can strike through the cover causing the body facing surface to be undesirably tacky.

Super Absorbent Fixation

In making Sample A, the adhesive of Example 1 was sprayed onto nonwoven using a Bayer & Otto Hand held spray gun. Three grams of a polyacrylate super absorbent polymer commercially available from Hoechst Celanese under the tradename Sanwet® IM-4500 was sprinkled on the adhesive surface having an area of about 4"x5". Sample B was made in a similar matter except the adhesive was sprayed onto release paper rather than nonwoven. A second layer of adhesive was sprayed on top of the SAP sandwiching the SAP between two adhesive layers. The total adhesive coating weight for Sample A was about 45 mg/in$^2$ and about 75 mg/in$^2$ for Sample B. Although the adhesive coat weight is substantially (as much as 10x) higher than the applicants anticipate would be used commercially, the examples are appropriate for demonstrating the unique properties of the adhesive of this invention. The adhesive coated SAP of Sample A and Sample B were then placed in a tray to containe overflow during absorption testing. A control sample was made by placing a 4"x5" piece of nonwoven in a tray and sprinkling the SAP on top in the absence of adhesive. A 100 ml buret was used to deliver 100 ml of 0.9 NaCl/ 0.04% Triton® X-100 (Fischer-Scientific) solution at a rate of 25 ml/minute. It took about 4 minutes for the SAP of the control sample to contain and absorb the fluid. The time for both Sample A and Sample B to contain and absorb the fluid was also 4 minutes, even in the presence of excess amounts of adhesive. After the fluid was absorbed, each sample was tipped at an angle of about 90°. Since the SAP of the control sample was not adhered, the SAP fell off. However, most of the SAP was adhered in place in Sample A and all the SAP was held in place in Sample B. After a 5 hour dwell time, Samples A and B were tipped again. Both continued to hold the SAP in place. Unexpectedly, the adhesive of Example 1 was able to maintain a bond with SAP in the presence of saline without interfering with the absorption rate of the SAP.

Blending Copolyesters

Examples 1 through 6 illustrate the distinct advantage of blending the copolyesters. The neat copolyesters having an intrinsic viscosity of about 28,000 cps or greater are not readily dispersible in ambient temperature tap water, meaning 1 g will not disperse in 100 ml of water unagitated in less than about 24 hours. Although the 0.2 IV copolyester is readily dispersible, it lacks cohesive strength. However, upon blending the copolyesters at the proper ratios, it is possible to significantly increase the strength of the resulting hot melt composition without sacrificing water dispersibility.

The onset of water dispersibility for the blended 0.4 IV material is between 100% 0.4 IV and the blend of Example 6 wherein the 0.2 IV material was combined with the 0.4 IV material at a ratio of 0.25:1. Since the viscosity of Example 6 is 27,000 cps, the applicants surmise that a 0.4 IV copolyester near the lower region of the viscosity range depicted in Table I may also be readily water dispersible. For the higher viscosity copolyesters wherein the intrinsic viscosity is about 0.6 or greater, the preferred ratio for blending with a 0.2 IV copolyester ranges from about 1:1 to about 2:1 wherein two parts of the 0.2 IV copolyester is combined with every one part of a higher viscosity copolyester. Alternatively, the water dispersibility of the higher viscosity copolyesters may be increased by increasing the concentration of the 5-sodiosulfoisophthalate in the polymer backbone.

Examples 2 through 6 may be useful compositions without further compounded. However, preferably the blended copolyesters are further combined with tackifiers and plasticizers to further improve processability and reduce cold flow tendencies. The resulting hot melt comprises at least about 25% copolyester in order to exhibit a lower contact angle and preferably at least about 50% to be readily dispersible in water. The resulting adhesive preferably has a viscosity less than about 12,000 cps at 300° F. to enable the adhesive to be applied at as low of application temperature as possible. This feature is critical for achieving acceptable viscosity stability during usage by the customer.

Blending Copolyesters with Conventional Hot Melts

Examples 7 through 9 depict the utility of blending a water dispersible copolyester with a conventional hot melt to increase the water responsiveness of the conventional hot melt adhesive. Examples 7 and 8 are construction adhesive blends whereas Example 9 is a positioning adhesive blend. HL-1280 and D-58 are both commercially available from H.B. Fuller.

The adhesives were coated and tested according to the methods described above. The resulting construction peel data and wet strength data were as follows:

|  | HL-1280 | Example 7 | Example 8 |
|---|---|---|---|
| Construction T-peel Data | | | |
| Multi-bead | 110 g* | 190 g (37) | 120 g (12) |
| Spiral Spray | 90 g* | 70 g (9) | 40 g (5) |
| Wet Strength T-peel Data | | | |
| Time to Failure | | | |
| Dry | >4,000 sec | | >4,000 sec |
| Water | >4,000 sec | | Failed at 300 sec |
| .9% Saline & | >4,000 sec | | >4,000 sec |

*Values represent a running average of historical values.

Examples 7 and 8 exhibited acceptable spray patterns and bonds with respect to HL-1280, a standard construction adhesive of the industry. Example 8 demonstrated dispersibility in water, yet was unaffected by synthetic body fluids. (0.9% saline/0.04% Triton® X-100).

The positioning adhesive of Example 9 was compared to unblended D-58. The results were as follows:

| Positioning T-peels | | |
|---|---|---|
|  | Example 9 | D-58 |
| Initial to Cotton | 210 g (34) | 188 g* |
| Stressed to Nylon | 100 g (22) | 212 g* |

*Values represent a running average of historical data.

Although the addition of the Eastman copolyester reduced the stressed T-peel value, no transfer was evident. Furthermore, the addition of a water dispersible copolyester enhances the hydophilicity with respect to deionized water as depicted below.

| Contact Angles | | | | |
|---|---|---|---|---|
|  | HL-1280 | Example 7 | D-58 | Example 9 |
| Deionized Water | | | | |
| Initial | 60° | 59° | 63° | 57° |
| After 5 min. | 37° | 35° | 43° | 24° |
| After 10 min | 20° | 2° | 23° | 0 |
| .9% NaCL/.04% Triton ® | | | | |
| Initial | 32° | 28° | 38° | 18° |
| After 5 min. | 14° | 14° | 14° | 0 |
| After 10 min | 8° | 3° | 0 | 0 |

TABLE I

Eastman AQ 1350 Polyester
Typical Physical Properties

| | |
|---|---|
| Form | Clear Solid |
| Density g/cm | 1.2 |
| Brookfield Viscosity | 10,000–100,000 cps @ 177° C.** |
| Inherent Viscosity | .2 to .65* |
| Ring and Ball Softening Point | 80–113° C. |
| Tensile Strength | .09 to .40 mPa |
| Elongation | 400–800% |
| Hydroxyl Number | 22 |
| Acid Number | 2 |

TABLE I-continued

Eastman AQ 1350 Polyester
Typical Physical Properties

| Inherent Viscosity | Brookfield Viscosity @ 177° C. (cps)** |
|---|---|
| .2 IV | less than 7,000 |
| .4 IV | about 28,000 to 40,000 |
| .6–.8 IV | about 40,000 to 100,000 |

*Applicants have also received a .8 IV sample.

TABLE II

24 Hour Ambient Temperature Dispersibility
(1g/100 ml of water, unagitated)

| .2 IV | 100% dispersed |
|---|---|
| .4 IV | softened/undispersed |
| .6 IV | undispersed |
| .8 IV | undispersed |
| Example 1 | 100% dispersed |
| Example 2 | 70% dispersed |
| Example 3 | 100% dispersed |
| Example 4 | 70% dispersed |
| Example 5 | 100% dispersed |
| Example 6 | 100% dispersed |
| Example 7 | 60% dispersed |
| Example 8 | 20% dispersed |
| Example 9 | 10% dispersed |

TABLE III

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| .2 IV Eastman | 44.8% | 50.0% | 66.6% | 50.0% | 66.6% | 80.0% | 70.0% | 50.0% | 50.0% |
| .4 IV Eastman | 30.0 | | | | | 20.0% | | | |
| .6 IV Eastman | | 50.0% | 33.4% | | 33.4% | | | | |
| .8 IV Eastman | | | | 50.0% | | | | | |
| Irganox 1010 | 0.2 | | | | | | 0.15 | | |
| Benzoflex 352 | 25.0 | | | | | | | | |
| 500 Process Oil | | | | | | | 9.1 | | |
| Kraton D 4158 | | | | | | | 3.8 | | |
| Vector 4211 | | | | | | | 1.3 | | |
| Unitac R100 | | | | | | | 15.65 | | |
| HL-1280 | | | | | | | | 50.0 | |
| D-58 | | | | | | | | | 50.0 |
| Viscosity @ 300° F. | 7125 cps | | | | | | | | |
| @ 325° F. | 3500 | | | | | | | | |
| @ 350° F. | | | | | | | 27,000 | | |
| 24 Hour Viscosity | 5925 (−17%) | | | | | | | | |

| Example # | 10 | 11 | 12 | 13 | 14 | 15 | 16 | 17 | 18 | 19 | 20 | 21 |
|---|---|---|---|---|---|---|---|---|---|---|---|---|
| Eastman AQ-1045 (.2 IV) | 60 | 54 | 56 | 70 | 70 | 81.7 | 79.7 | | 81.2 | 79.4 | 79.4 | 81.4 |
| Eastman AQ-1350 (.4 IV) | | | | | | | | 81.7 | | | | |
| Kraton ® D1117 | 40 | 36 | 12 | 10 | 15 | 8 | 4 | 8 | 4 | 5 | 5 | 8 (D1124) |
| Kraton ® D6428 | | | 12 | 10 | 15 | | 4 | | | | | |
| Solprene 1205 | | | | | | | | | 4 | | | |
| Eastoflex E1060S | | | | | | | | | | 5 | | |
| Rextac RT2215 | | | | | | | | | | | 5 | |
| Benzoflex ® 988 | | 10 | 10 | | 10 | 12 | 10 | 10 | 10 | 10 | 10 | 10 |
| Irganox 1010 | | | | | 0.3 | 0.3 | 0.3 | 0.3 | 0.6 | 0.6 | 0.6 | |
| Repulpability | F | F | F | P | F | P | | P | | | | |

TABLE III-continued

| Viscosity (cPs) | | | | |
|---|---|---|---|---|
| @ 300° F. | 9062 | | | |
| @ 325° F. | 4525 | | | |
| @ 350° F. | 3100 | | | |
| Loop Tack (oz/in) (average of 3) | 42.3 | 11.7 | 9.3 | 23.7 |
| 180° Peel (lb/in) (average of 3) | 4.2 | 1.8 | 3.8 | 4.3 |

Examples 10–18 exhibit the utility of blending a block copolymer with the water dispersible copolyester. Surprisingly, block copolymers can be employed at levels up to 20% by weight without affecting the repulpability. Example 17 was used to bond labelstock onto a PET bottle. The adhesive did not produce a fiber tearing bond immediately. However, after 2 hours a fiber tearing bond was achieved. The applicants surmize the adhesion was increased due to the adhesive absorbing moisture from the laboratory atmosphere. Example 17 was also found to exhibit good adhesion to glass, metal cans, and fabric.

What is claimed is:

1. A hot melt adhesive composition comprising:
   (a) from about 25 to about 90 percent by weight of at least one water dispersible copolyester;
   (b) from about 5 to about 50 percent by weight of a plasticizer wherein said plasticizer is solid at ambient temperature; and
   (c) from 0 to about 70 percent by weight of a compatible tackifier;
   wherein said adhesive composition is dispersible in water.

2. The adhesive composition of claim 1 wherein said plasticizer recrystallizes in the adhesive composition.

3. The adhesive composition of claim 1 wherein said plasticizer is a cyclohexane dimethanol dibenzoate compound.

4. The adhesive of claim 1 wherein said adhesive bonds at least one super absorbent polymer.

5. The hot melt adhesive of claim 1 wherein the viscosity of said adhesive is less than about 12,000 cps at 300° F.

6. The adhesive of claim 1 wherein said adhesives resists cold flow.

7. The hot melt adhesive of claim 1 wherein at least one of said water dispersible copolyesters has a viscosity less than about 7,000 cps at 177° C.

8. A hot melt adhesive composition comprising at least about 50 percent by weight of a blend of at least two branched water dispersible copolyesters wherein at least one of said copolyesters has a viscosity of less than about 7,000 cps at 177° C. and at lest one of said copolyesters has a viscosity of greater than about 28,000 cps at 177° C.

9. The hot melt adhesive of claim 8 wherein said first copolyester and said second copolyester are combined at a weight ratio of from about 0.25:1 to about 2:1.

10. The hot melt adhesive of claim 8 wherein said adhesive is water dispersible.

11. A pressure sensitive adhesive comprising:
    (a) from about 25 to about 90 percent by weight of at least one water dispersible copolyester;
    (b) from about 5 to about 50 percent by weight of a plasticizer; and
    (c) from about 3 to about 20 percent by weight of a block copolymer;
    wherein said adhesive is repulpable.

* * * * *

UNITED STATES PATENT AND TRADEMARK OFFICE
CERTIFICATE OF CORRECTION

PATENT NO. : 6,448,463 B1  Page 1 of 1
DATED : September 10, 2002
INVENTOR(S) : Carolyn A. Fischer et al.

It is certified that error appears in the above-identified patent and that said Letters Patent is hereby corrected as shown below:

Title page,
Item [63], Related U.S. Application Data, "Continuation-in-part of application No. 08/562,038, filed on Nov. 22, 1995, now Pat. No. 6,087,990" should be -- Continuation-in-part of application No. 08/562,038 filed on Nov. 22, 1995, now Pat. No. 6,087,550 --

Column 1,
Lines 5-6, "U.S. Pat. No. 6,087,990" should be -- U.S. Pat. No. 6,087,550 --

Column 9,
Lines 39-40, "the film should contain at least 50o water dispersible materials," should be -- the film should contain at least 50% water dispersible material --

Column 10,
Line 55, "containe overflow during" should be -- contain overflow during --

Signed and Sealed this

Twenty-fourth Day of June, 2003

JAMES E. ROGAN
*Director of the United States Patent and Trademark Office*